(12) United States Patent
Kelman et al.

(10) Patent No.: US 8,148,176 B2
(45) Date of Patent: Apr. 3, 2012

(54) METHODS FOR DISTINGUISHING A SET OF HIGHLY DOPED REGIONS FROM A SET OF LIGHTLY DOPED REGIONS ON A SILICON SUBSTRATE

(75) Inventors: Maxim Kelman, Mountain View, CA (US); Giuseppe Scardera, Sunnyvale, CA (US)

(73) Assignee: Innovalight, Inc., Sunnyvale, CA (US)

( * ) Notice: Subject to any disclaimer, the term of this patent is extended or adjusted under 35 U.S.C. 154(b) by 2 days.

(21) Appl. No.: 12/544,713

(22) Filed: Aug. 20, 2009

(65) Prior Publication Data

US 2011/0045612 A1 Feb. 24, 2011

(51) Int. Cl.
*H01L 21/00* (2006.01)
(52) U.S. Cl. .................. 438/7; 438/14; 257/E21.53
(58) Field of Classification Search ............. 438/7, 14; 257/E21.53
See application file for complete search history.

(56) References Cited

U.S. PATENT DOCUMENTS

| | | | |
|---|---|---|---|
| 3,641,332 A | 2/1972 | Reick et al. | |
| 4,534,804 A | 8/1985 | Cade | |
| 5,354,695 A | 10/1994 | Leedy | |
| 5,610,089 A * | 3/1997 | Iwai et al. | 438/210 |
| 7,063,991 B1 * | 6/2006 | Zhao et al. | 438/14 |
| 7,800,081 B2 * | 9/2010 | Moffatt et al. | 250/492.2 |
| 2005/0122525 A1 | 6/2005 | Borden et al. | |
| 2006/0115956 A1 | 6/2006 | Raval et al. | |
| 2006/0222592 A1 | 10/2006 | Burda | |
| 2009/0017606 A1 | 1/2009 | Fath et al. | |
| 2009/0161724 A1 * | 6/2009 | Timans | 374/161 |

OTHER PUBLICATIONS

Falk, R. A., "Near IR Absorption in Heavily Doped Silicon—An Empirical Approach," OptoMetrix, Inc., Renton, Washington, Proc. 26th International Symposium for Testing and Failure Analysis., 2000, pp. 1-7.

Isenberg, J. et al., "Free carrier absorption in heavily doped silicon layers," Applied Physics Letters, vol. 84, No. 13, 2004, pp. 2265-2267.

Isenberg, J. et al., "Sheet Resistance Imaging (SRI)—A Contactless and Spatially Resolved Method for the Determination of Doping Inhomogeneities," presented at the 20th European Photovoltaic Solar Energy Conference and Exhibition, Jun. 6-10, 2005, Barcelona, Spain, 4 pages.

Schubert, M. C. et al., "Spatially resolved lifetime imaging of silicon wafers by measurement of infrared emission," Journal of Applied Physics, vol. 94, No. 6, 2003, pp. 4139-4143.

Vanecek, M. et al., "Light Trapping and Optical Losses in Microcrystalline Si and Micromorph Solar Cells," presented at 3rd World Conference on Photovoltaic Energy Conversion, May 11-18, 2003, Osaka, Japan, 6 pages.

International Search Report and Written Opinion dated Oct. 5, 2010, in corresponding PCT/US2010/45614, 7 pages.

* cited by examiner

*Primary Examiner* — Walter L Lindsay, Jr.
*Assistant Examiner* — Stanetta Isaac
(74) *Attorney, Agent, or Firm* — Foley & Lardner LLP (57) ABSTRACT

A method of distinguishing a set of highly doped regions from a set of lightly doped regions on a silicon substrate is disclosed. The method includes providing the silicon substrate, the silicon substrate configured with the set of lightly doped regions and the set of highly doped regions. The method further includes illuminating the silicon substrate with an electromagnetic radiation source, the electromagnetic radiation source transmitting a wavelength of light above about 1100 nm. The method also includes measuring a wavelength absorption of the set of lightly doped regions and the set of heavily doped regions with a sensor, wherein for any wavelength above about 1100 nm, the percentage absorption of the wavelength in the lightly doped regions is substantially less than the percentage absorption of the wavelength in the heavily doped regions.

10 Claims, 7 Drawing Sheets

METHODS FOR DISTINGUISHING A SET OF HIGHLY DOPED REGIONS FROM A SET OF LIGHTLY DOPED REGIONS ON A SILICON SUBSTRATE

FIELD OF DISCLOSURE

This disclosure relates in general to silicon substrates and more specifically to methods for distinguishing a set of highly doped regions from a set of lightly doped regions on a silicon substrate.

BACKGROUND

Semiconductors form the basis of modern electronics. Possessing physical properties that can be selectively modified and controlled between conduction and insulation, semiconductors are essential in most modern electrical devices (e.g., computers, cellular phones, photovoltaic cells, etc.). Group IV semiconductors generally refer to those first four elements in the fourth column of the periodic table: carbon, silicon, germanium and tin.

The ability to deposit semiconductor materials using non-traditional semiconductor technologies such as printing may offer a way to simplify the fabrication process and hence reduce the cost of many modern electrical devices such as solar cells. Like pigment in paint, these semiconductor materials are generally formed as microscopic particles, such as nanoparticles, and temporarily suspended in a colloidal dispersion that may be later deposited on a substrate.

Nanoparticles are generally particles with at least one dimension less than 100 nm. In comparison to a bulk material (>100 nm) which tends to have constant physical properties regardless of its size (e.g., melting temperature, boiling temperature, density, conductivity, etc.), nanoparticles may have physical properties that are size dependent, such as a lower sintering temperature.

In general, nanoparticles may be produced by a variety of techniques such as evaporation (S. Ijima, Jap. J. Appl. Phys. 26, 357 (1987)), gas phase pyrolysis (K. A Littau, P. J. Szajowski, A. J. Muller, A. R. Kortan, L. E. Brus, J. Phys. Chem. 97, 1224 (1993)), gas phase photolysis (J. M. Jasinski and F. K. LeGoues, Chem. Mater. 3, 989 (1991)), electrochemical etching (V. Petrova-Koch et al., Appl. Phys. Lett. 61, 943 (1992)), plasma decomposition of silanes and polysilanes (H. Takagi et al, Appl. Phys. Lett. 56, 2379 (1990)), high pressure liquid phase reduction-oxidation reaction (J. R. Heath, Science 258, 1131 (1992)), etc.

In general, a solar cell converts solar energy directly to DC (direct current) electric energy. Configured as a photodiode, a solar cell permits light to penetrate into the vicinity of metal contacts such that a generated charge carrier (electrons or holes—a lack of electrons) may be extracted as current. And like most other diodes, photodiodes are formed by combining p-type and n-type semiconductors to form a junction. After the addition of passivation and anti-reflection coatings, a layer acting as back surface field and metal contacts (fingers and busbar on the emitter, and pads on the back of the absorber) may be added in order to extract generated carriers. Emitter dopant concentration, in particular, must be optimized for both carrier collection and for contact with the metal electrodes.

In general, a low concentration of dopant atoms within an emitter region will tend result in both a low recombination of carriers (and thus higher solar cell efficiencies—the percentage of solar power that is converted to electricity) and poor electrical contact to metal electrodes. In contrast, a high concentration of dopant atoms will tend to have the opposite result. That is good electrical contact to metal electrodes, but high recombination of carriers (and thus reduced solar cell efficiency). Often, in order to reduce manufacturing costs, a single dopant diffusion is generally used to form the emitter, with a doping concentration selected as a compromise between reducing recombination and improving ohmic contact formation. Consequently, a sub-optimal solar cell efficiency is achieved.

One solution is the use of a selective (or dual-doped) emitter. A selective emitter generally uses a first lightly doped region optimized for low recombination, and a second heavily doped region pattern (of the same dopant type) optimized for low resistance ohmic contact formation. Selective emitters are commonly formed with either multiple diffusion steps in conjunction with diffusion blocking layers, or else formed with multiple dopant sources.

However, since the principal variation between such regions is a difference in dopant atomic concentration, there is generally no visible contrast between the highly and lightly doped regions. Consequently, reliably aligning (axial and/or angular) a metal contact pattern onto the formed highly doped region pattern may be problematic.

Likewise, a similar alignment problem may occur in alternative solar cell configurations, such as a back-contact solar cell. Configured with a set of non-visible counter-doped highly doped patterns, a set of corresponding inter-digitated metal contact patterns must also be reliably aligned.

However, proper alignment generally requires the selection of a reference point and a rotation angle that are used to translate and rotate the metal pattern prior to placing it on the solar cell substrate. A first approach involves the creation of artificial reference points or fiducial marks from which both the heavily doped regions and the metal contacts are deposited. However, the use of fiducial marks generally requires an additional processing step (and tool). Furthermore, since both patterns are independently placed relative to the fiducial marks (and not to each other), tolerance errors are additive. That is, first the heavily doped pattern is defined relative to the fiducial marks within a certain tolerance followed by the metal deposition also positioned relative to the fiducial marks with a different tolerance.

An alternative method involves alignment to the substrate edge, which generally requires that the substrate orientation be kept constant (to minimize errors caused by variations in substrate sizes) between subsequent deposition steps. However, for sequential deposition steps, each deposition tool would need to base all calculations on the same exact edge locations, which may be problematic particularly in high throughput manufacturing. Furthermore, since substrate edge geometries tend to be non-ideal and poorly defined, alignment accuracy may also be problematic.

In view of the foregoing, there is a desire to provide methods distinguishing a set of highly doped regions from a set of lightly doped regions on a silicon substrate.

SUMMARY

The invention relates, in one embodiment, to a method of distinguishing a set of highly doped regions from a set of lightly doped regions on a silicon substrate is disclosed. The method includes providing the silicon substrate, the silicon substrate configured with the set of lightly doped regions and the set of highly doped regions. The method further includes illuminating the silicon substrate with an electromagnetic radiation source, the electromagnetic radiation source transmitting a wavelength of light above about 1100 nm. The method also includes measuring wavelength absorption of the set of lightly doped regions and the set of heavily doped regions with a sensor, wherein for any wavelength above 1100 nm, the percentage absorption of the wavelength in the lightly doped regions is substantially less than the percentage absorption of the wavelength in the heavily doped regions.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

As previously stated, it is difficult to distinguish a set of highly doped regions from a set of lightly (or undoped) regions. Since a silicon substrate is generally opaque in the visible spectrum (about 300 nm to about 700 nm), pattern alignment approaches must generally rely on reflected visible light. However, as light reflection is reduced to optimize solar cell efficiency, visual pattern alignment relying on reflected light becomes problematic.

In an advantageous manner, the transmission spectra of wavelengths above about 1100 nm (infrared radiation or IR) may be measured in order to distinguish between highly doped regions and lightly doped regions on a silicon substrate surface, and thus allow for the reliable deposition of a set of metal contact patterns on the highly doped regions. In one configuration, a broad spectrum radiation source, (such as a quartz lamp) may radiate toward one side of the substrate, while an electromagnetic radiation measurement device (such as a video camera with appropriate CCD chips) would be positioned on the alternate side of the substrate.

In general, undoped silicon is an indirect-bandgap semiconductor with a bandgap of approximately 1.1 eV, which corresponds to a wavelength of about 1100 nm (nanometer) or about 1.1 μm (micrometer). In general, electromagnetic radiation with a wavelength shorter than about 1.1 μm tends to be absorbed by the silicon substrate, whereas electromagnetic radiation with longer wavelengths (less energy) will generally not be absorbed.

The addition of dopants, as previously described, tends to both moderately change the band structure of the crystal lattice of the silicon substrate (by decreasing the bandgap), and also add electronic states into the bandgap (thus increasing free-carrier absorption of sub-bandgap photons). For example, silicon substrates used for solar cell manufacturing are generally not strongly doped, with a resistivity in the range of about 0.1 to about 10 ohm·cm (corresponding to a dopant concentration of $10^{14}$ to $10^{17}$ atoms/cm$^3$). In contrast, doped emitter and contact regions generally have significantly higher dopant concentration (typically in the range of $10^{18}$-$10^{20}$ atoms/cm$^3$).

Consequently, the addition of dopants to the silicon substrate will tend to increase absorption of photons in those doped areas that have less energy than the bandgap (wavelengths greater than about 1.1 microns). Thus, the absorption of differing doping levels may be used to identify and align to highly doped regions in solar cells using transmitted infrared radiation.

For example, prior to the deposition of metal contacts (metallization), a solar cell with highly doped regions may be placed on an IR-transparent table positioned above a white light (wide-band) radiation source (i.e., halogen tungsten lamp, etc.). The radiation may then go through the transparent substrate support structure. Consequently the visible and near-visible portion of the light spectrum may be reflected or absorbed by the silicon wafer, whereas the IR portion of the spectrum (greater than about 1100 nm) will generally be transmitted. By placing an IR sensitive camera, such as a CCD camera (with for example an InGaAs detector) above the wafer, a 2-D image of IR light intensity transmitted through the silicon substrate will be captured.

In addition, although lightly doped silicon substrate bulk may absorb a minimal fraction of the IR light, a greater number of IR photons will be absorbed by the higher doped field emitter regions. The areas of highest IR absorption will tend to correspond to the areas of highest doping density, corresponding to the same regions over which the metal pattern needs to be placed. In general, in the 2-D camera image, these areas would tend to appear the darkest, with lighter doped field emitter regions appearing brighter in the camera image.

In an alternate configuration, an IR radiation source may be used instead of the wide-band light. Consequently, the portion of the light that is absorbed by the wafer is not present at all.

Figure 1:
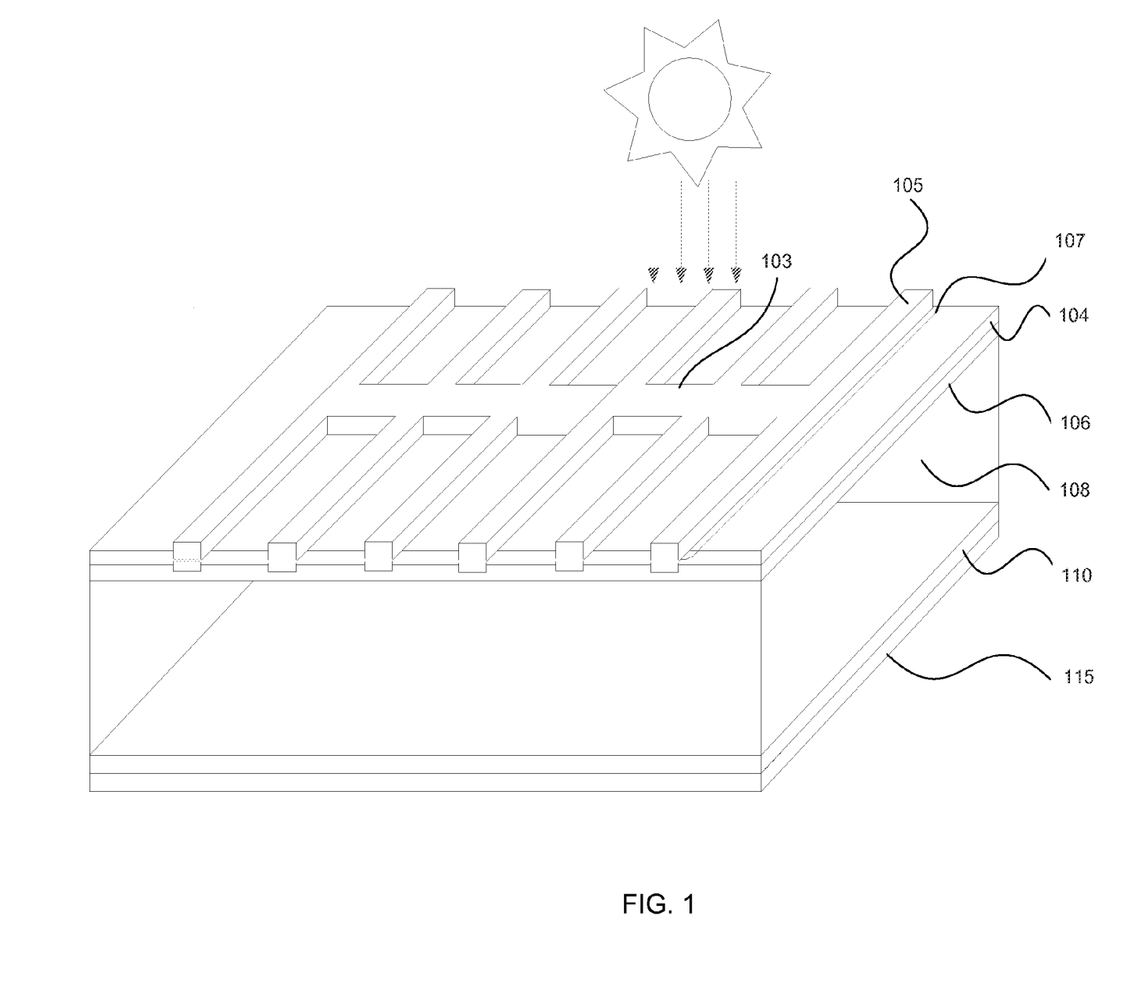
FIG. 1 shows a simplified diagram of a front-contact solar cell with a selective emitter, in accordance with the invention.

FIG. 1 shows a simplified diagram of a front-contact solar cell with a selective emitter, in accordance with the invention. Comprising lightly doped region 106 and heavily doped region 107, the selective emitter layer may be p-type (e.g., boron) or n-type (e.g., phosphorous) and could be formed by various methods, which include but are not limited to gas phase diffusion (such as e.g. using POCl$_3$ gas as phosphorous source or BBr$_3$ as boron source), solid source diffusion, or inline processes which typically use liquid dopant sources such as phosphoric acid.

Above and in electrical contact with the emitter 106 (which is also typically coated with an antireflection coating 104) is a front metal contact, comprising a set of fingers 105 (here with a width of about 100 um silver) and a set of busbars 103. Typically made out of printed silver paste, the front metal contact is optimized to extract the charge carriers (here electrons) created in the silicon substrate when light is absorbed.

The front metal contact is also typically configured with a reduced horizontal surface area (thus minimizing losses due to shading, which tends to reduce the generated current), and an increased cross-sectional volume (thus reducing the series resistance of the device, which tends to increase the efficiency of the device).

In general, untreated silicon substrates often reflect more than 30% of incident light. Consequently, in order to reduce this reflected energy and thus directly improve efficiency, the silicon substrate is generally textured and optimized with anti-reflective coatings 104 (e.g., silicon nitride (SiNx), etc.). In addition, anti-reflective coating 104 also helps passivate the surface of emitter 106, minimizing both contamination of the substrate bulk from external sources, as well as substantially reducing minority carrier recombination caused by dangling Si bonds or imperfections in the doped substrate 108 surface.

Figure 2:
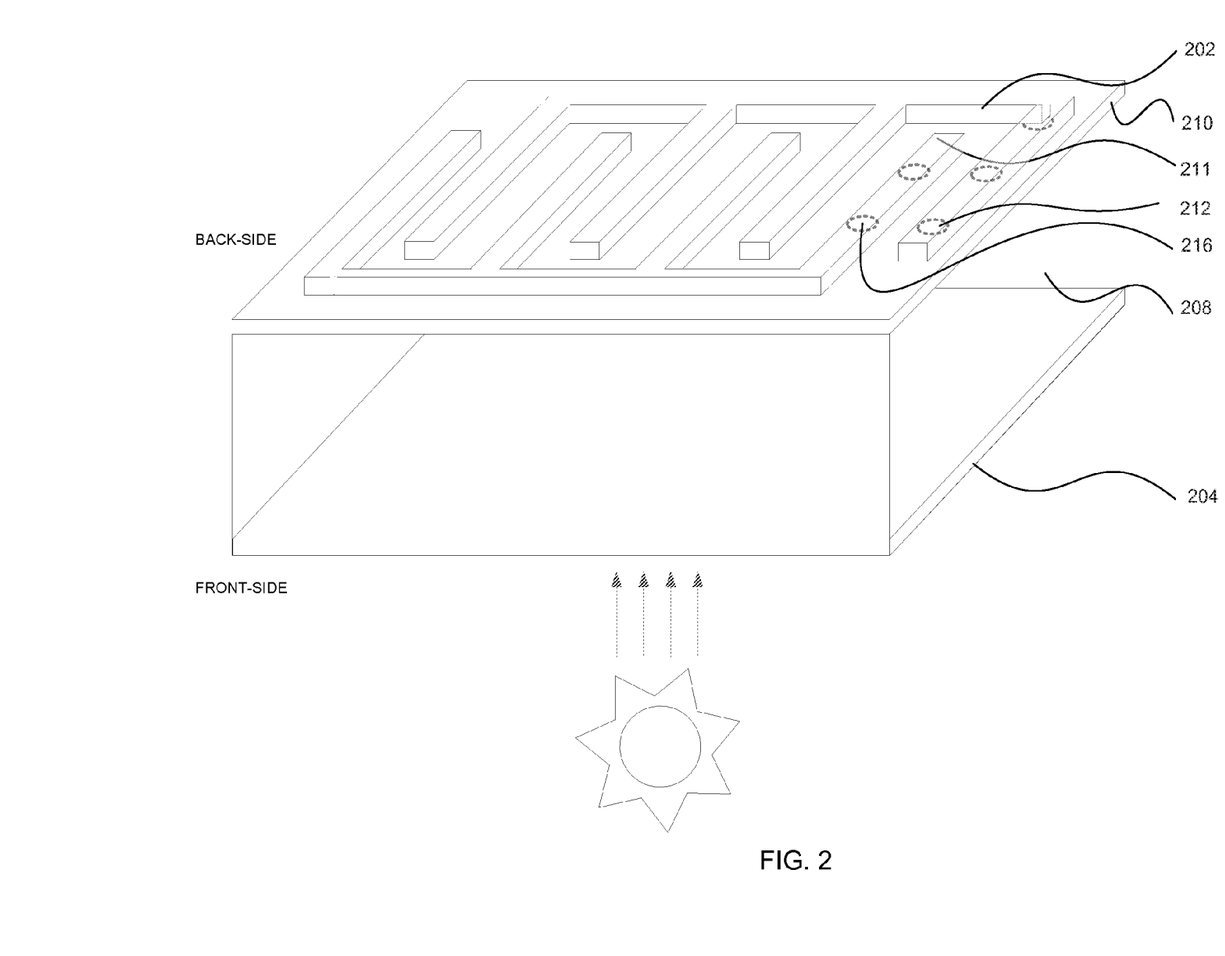
FIG. 2 shows a simplified diagram of a back contact solar cell, in accordance with the invention.

FIG. 2 shows a simplified diagram of a back contact solar cell, in accordance with the invention. Unlike front-contact solar cells as shown in FIG. 1, back-contact solar cells generally have both the emitter and the BSF, and thus the corresponding metal contacts, on the rear of the solar in an interdigitated configuration. Consequently, front-side shading losses are substantially eliminated which tends to improve overall solar cell efficiency.

In a common configuration, a set of p-type (emitter) regions 212 and a set of n-type base contact regions 216 are diffused into an n-type (phosphorous doped) silicon substrate 208. Optionally, a surface passivation layer 210 of silicon nitride or silicon oxide can be deposited on the back side of the surface. In order to extract the charge carriers, an emitter metal contact 202 is deposited over the set of p-type regions 212, and a base metal contact 211 is deposited over the set of n-type regions 213. In addition, a front-side layer 204 comprising an FSF (front-surface field) and an anti-reflective coating (as previously described) is also deposited.

Figure 3:
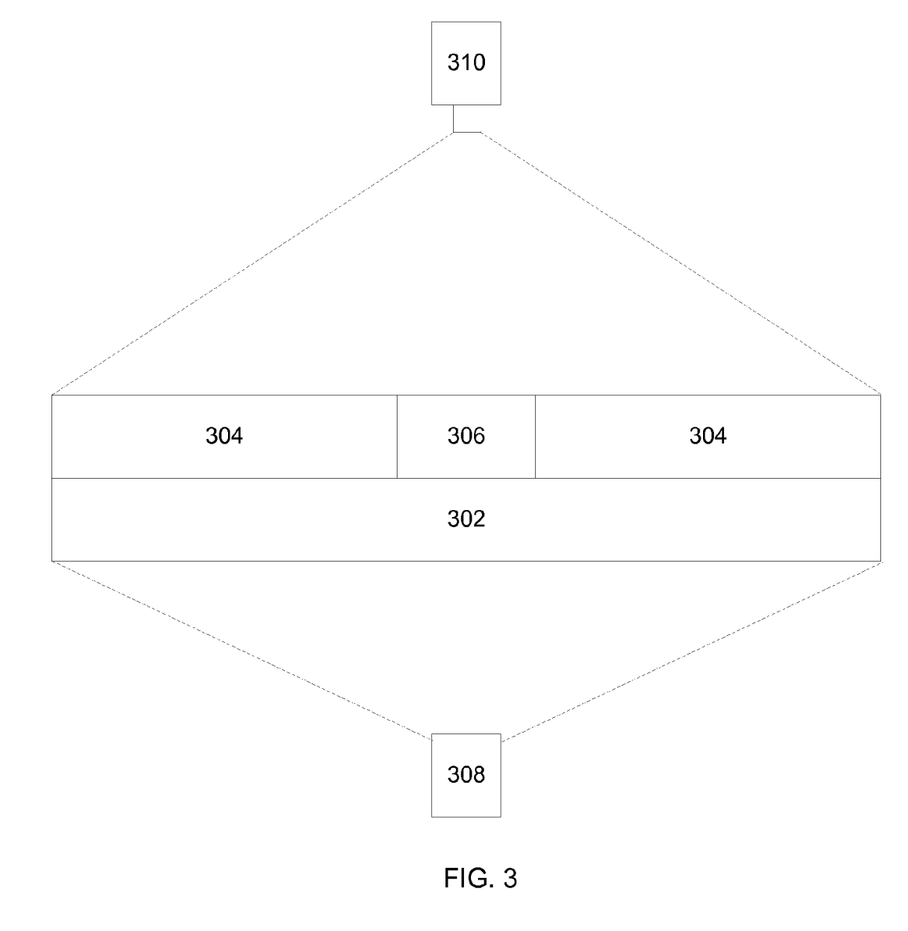
FIG. 3 shows a simplified diagram of the doped regions of a solar cell, as shown in FIGS. 1 and 2, in accordance with the invention.

FIG. 3 shows a simplified diagram of the doped regions of a solar cell, as shown in FIGS. 1 and 2, in accordance with the invention. Region 302 is generally the lightly doped region of the silicon substrate bulk. Regions 304 are the lightly doped regions of the selective emitter. And region 306 is the heavily doped region of the selective emitter. Consequently, in order to measure absorption and thus dopant concentration, an electromagnetic radiation source 308 (configured to transmit radiation in at least one wavelength of light above about 1100 nm) is positioned opposite the heavily doped region 306, while the electromagnetic radiation sensor 310 is positioned facing the heavily doped region 306. Below about 1100 nm, all the transmitted radiation would generally be absorbed by the silicon substrate bulk. In addition, although a sensor may be used to measure wavelengths of light above about 1700 nm, the cost is generally prohibitive. In addition, positions of the light source and detector can be reversed without impacting the performance of the method.

EXAMPLE 1

Figure 4A:
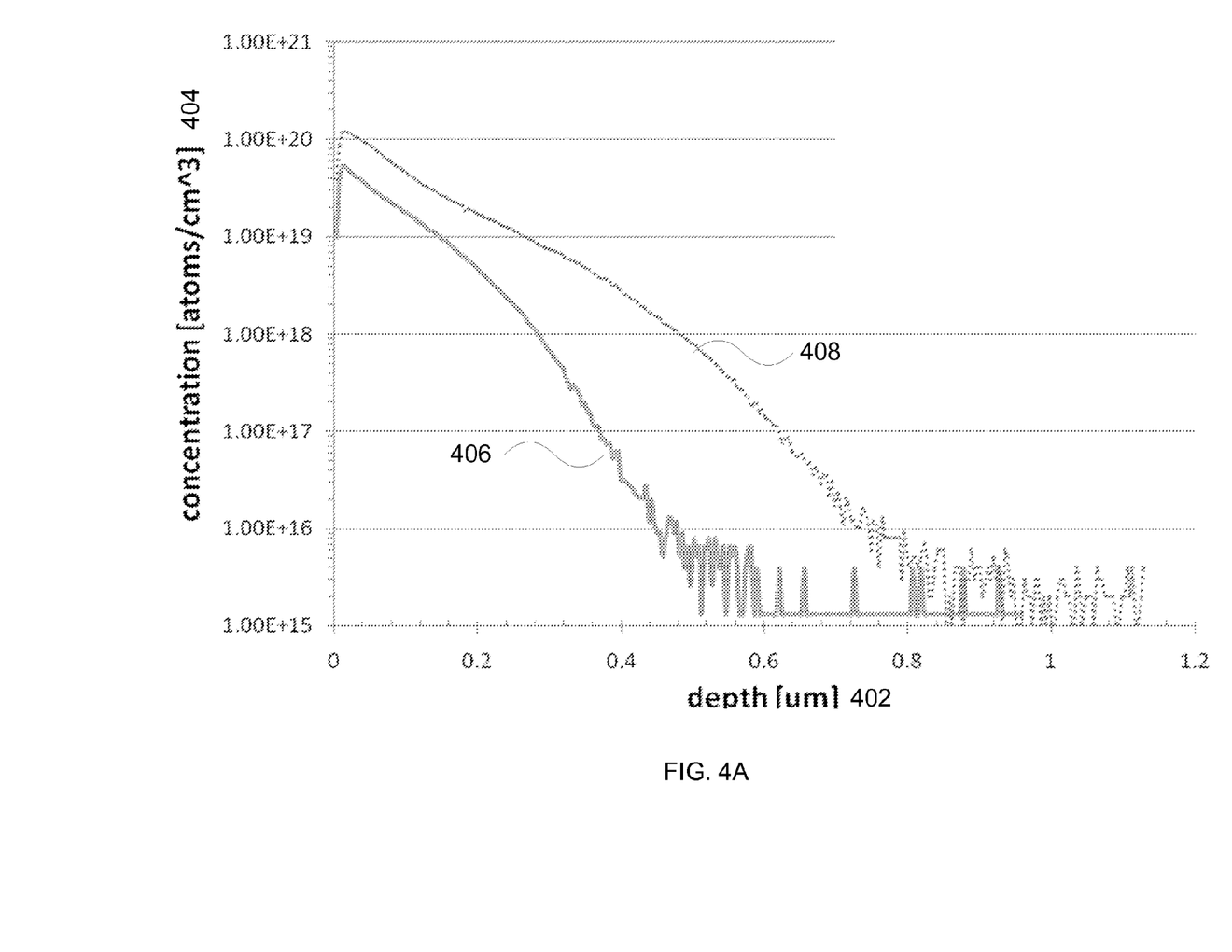
FIGS. 4A-B show a set of diagrams of the dopant concentration depth profiles and the corresponding transmission of infrared (IR) electromagnetic radiation, in accordance with the invention.
Figure 4B:
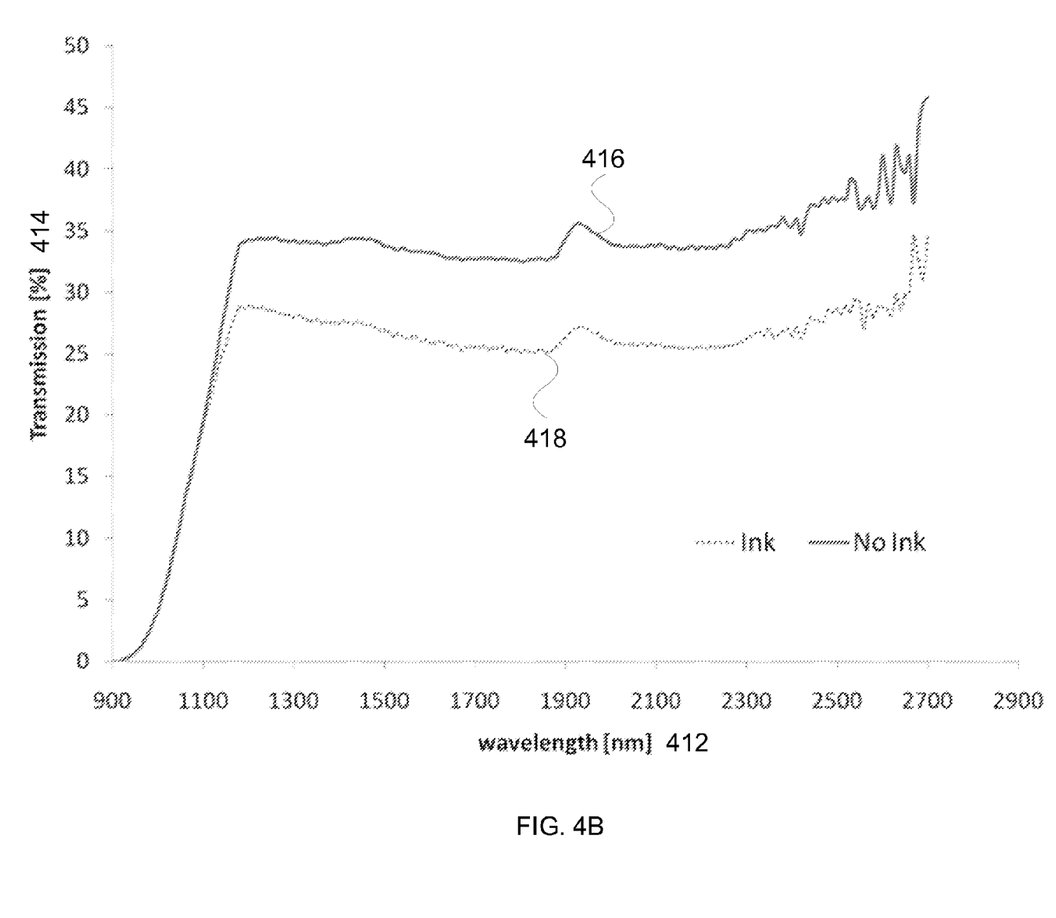

Referring to FIGS. 4A-B, a set of diagrams showing the dopant concentration depth profiles and the corresponding transmission of infrared (IR) electromagnetic radiation spectra through two locations on a substrate with different doping strengths.

FIG. 4A shows a simplified diagram of dopant concentration as a function of depth for a silicon substrate partially processed with a silicon nanoparticle ink in a POCl$_3$ diffusion furnace, in accordance with the invention. Along the horizontal axis 402 is depth in μm from the silicon substrate surface, while on the vertical axis 404 is shown phosphorous dopant concentration in atoms/cm$^3$.

As previously described, a nanoparticle is a microscopic particle with at least one dimension less than 100 nm. The term "Group IV nanoparticle" generally refers to particles having an average diameter between about 1 nm to 100 nm, and composed of silicon, germanium, carbon, or combinations thereof. The term "Group IV nanoparticle" also includes Group IV nanoparticles that are doped.

However, because of their small size, nanoparticles also tend to be difficult to manipulate. Consequently, in an advantageous manner, assembled nanoparticles may be suspended in a colloidal dispersion or colloid, such as an ink, in order to transport and store the nanoparticles. Generally, colloidal dispersions of Group IV nanoparticles are possible because the interaction of the particle surface with the solvent is strong enough to overcome differences in density, which usually result in a material either sinking or floating in a liquid. That is, smaller nanoparticles disperse more easily than larger nanoparticles.

A silicon nanoparticle ink may be deposited in a pattern on a silicon substrate surface, such that in a POCl$_3$ diffusion furnace, both a set of lightly doped regions and a set of heavily doped regions may be formed. In the case of a selective emitter, both a lightly doped region with sheet resistance of between about 90 Ohm/sq to about 120 Ohm/sq may be formed and a heavily doped region (of the same dopant type) with a sheet resistance may be formed between about 30 Ohm/sq to about 60 Ohm/sq.

A film of phosphorous-doped silicon nanoparticles (about 200-400 nm in thickness) was deposited as square silicon ink patches on saw-damage etched substrate. The substrate was baked at 600° C., followed by POCl$_3$ diffusion at 725° C. for 35 minutes with a drive-in and oxidation step at 975° C. for 15 minutes. Ink patches were then chemically etched away (and non-visible) by dipping the sample in a buffered oxide etch (BOE) solution for 5 minutes. As a result, the ink patches were invisible to the human eye.

Plot 406 shows the depth-dependent dopant concentration for the substrate area that was not covered with a silicon nanoparticle ink, while plot 408 shows the dopant concentration for the substrate area that was covered with a silicon nanoparticle ink as a function of distance away from the wafer surface The resultant surface concentrations of phosphorus near the substrate surface were nominally about $10^{20}$ cm$^{-3}$ and about $10^{19}$ cm$^{-3}$ in ink (408) and non-ink (406) covered areas, respectively. As can be seen, the dopant concentration in ink-covered regions at any given depth is substantially greater than the corresponding dopant concentration where ink was not substantially present.

FIG. 4B shows the transmission of infrared (IR) electromagnetic radiation through the wafer of FIG. 4A. Along the horizontal axis 412 is shown wavelength in nm, while on the vertical axis 414 is shown transmission percentage as measured with a spectrophotometer scanning the wavelength range above about 900 nm.

Plots 416 and 418 show percentage of light transmitted through the lightly and highly doped regions of the solar cell. As expected, in both cases, transmission of light goes to zero for light with wavelength below about 1.1 μm (micrometers), corresponding to bandgap absorption of light by the silicon wafer itself. For wavelengths greater than about 1100 nm, absorption and transmission generally depends on sub-band gap light absorption which is controlled by the doping level in the surface layer.

Plot 416, corresponding to dopant concentration plot 406 in FIG. 4A, shows the transmission percentage across a wavelength spectrum range for the substrate area that was not covered with a silicon nanoparticle ink.

Likewise, Plot 418, corresponding to dopant concentration plot 408 in FIG. 4A, shows the transmission percentage across a wavelength spectrum range for the substrate volume that was covered with a silicon nanoparticle ink.

As can be seen, the ink spectra of plot 418 exhibits reduced transmission across a wavelength range above about 1100 nm, consistent with increased absorption due to the heavier dopant concentration in these areas. For example, at a wavelength of 1800 nm, approximately 25% of the incident photons are transmitted through the heavily doped area, whereas 32% of the incident photons are transmitted though the lightly doped region. As seen by a 2-D IR (infrared) sensitive camera, the lighter doped region would appear about 30% brighter.

Figure 5:
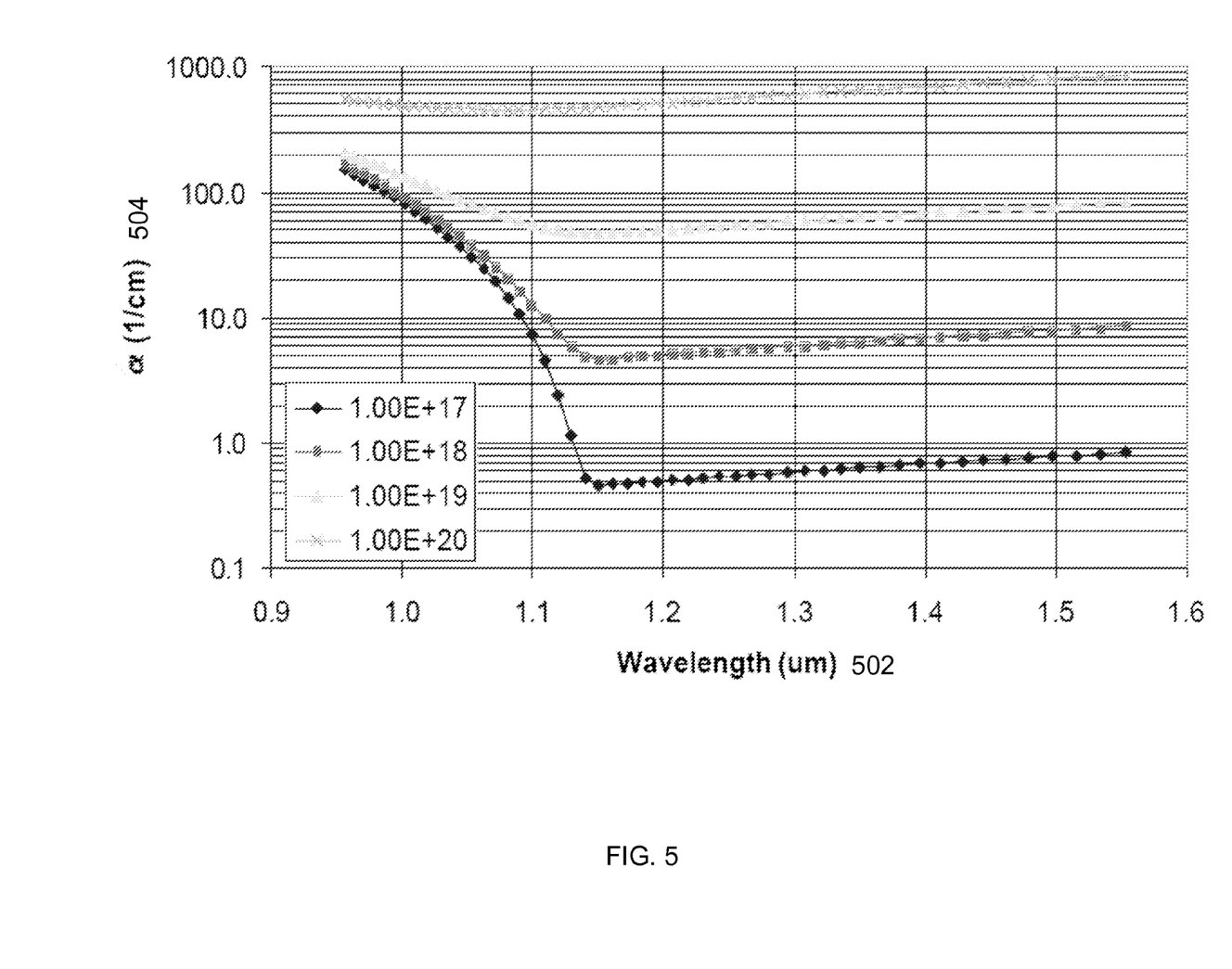
FIG. 5 shows an empirical model of absorption coefficient versus wavelength for various dopant concentrations in a silicon substrate.

FIG. 5 shows an empirical model of absorption coefficient versus wavelength for various dopant concentrations in a silicon substrate. [R. Aaron Falk, *Near IR Absorption in Heavily Doped Silicon—An Empirical Approach*, OptoMetrix, Inc. (ISTFA) International Symposium for Testing and Failure Analysis 2000]. Absorption coefficient $\alpha$ in units of 1/cm is shown on vertical axis 504, while wavelength in $\mu$m is shown along the horizontal axis 502. For wavelengths greater than the bandgap of silicon (1.1 $\mu$m), there is significant increase in absorption for increasing doping concentration, consistent with the results presented in FIG. 4.

Figure 6:
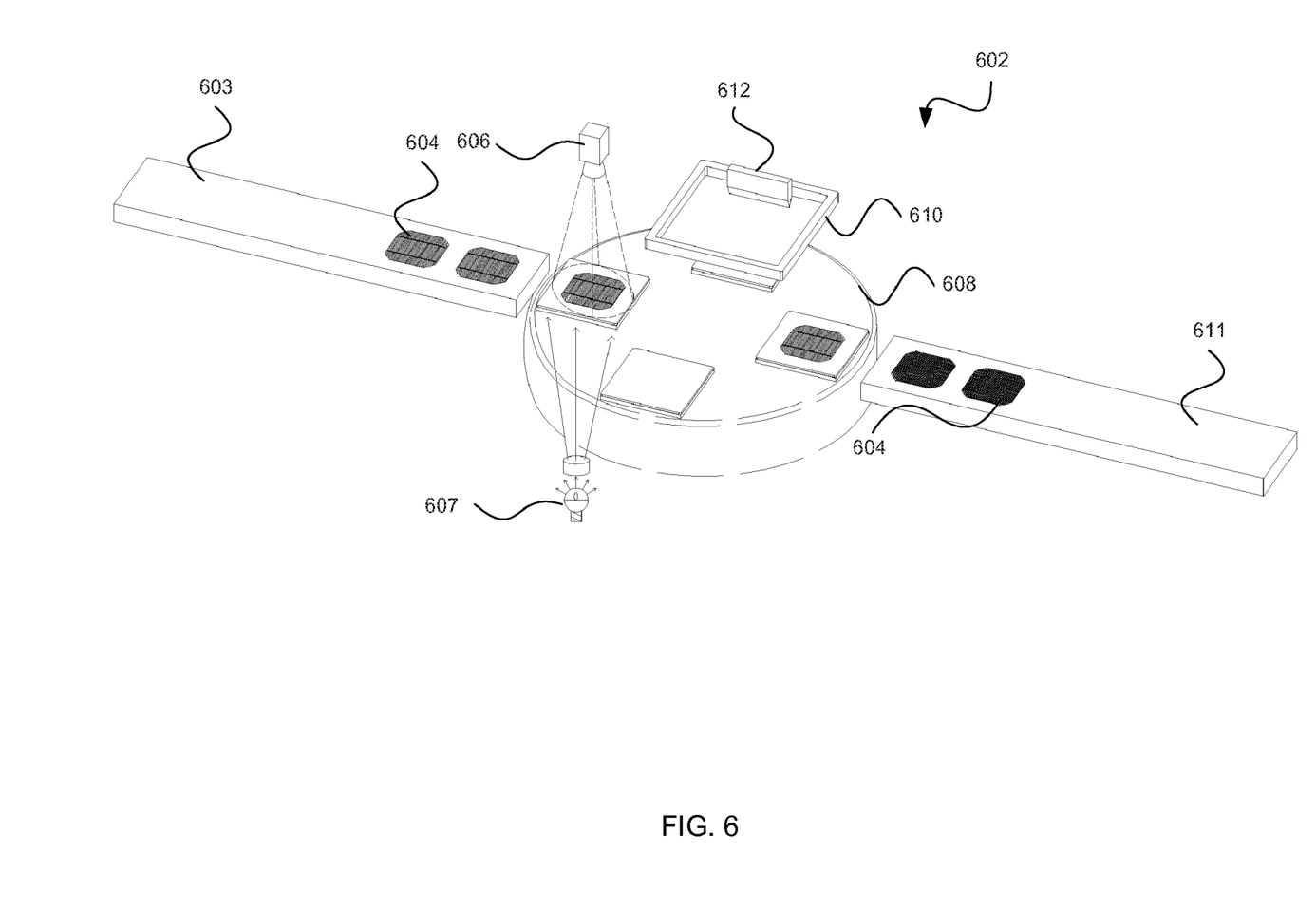
FIG. 6 shows a simplified diagram of an apparatus for superimposing a set of metal contacts on a set of highly doped regions on a crystalline solar cell substrate, in accordance with the invention.

FIG. 6, a simplified diagram of an apparatus for superimposing a set of metal contacts on a set of highly doped regions on a crystalline solar cell substrate in accordance with the invention.

Initially, a solar cell substrate 604 with a set of highly doped regions, such as for a selective emitter or a back-contact solar cell, is positioned on a substrate intake transport apparatus 603 (e.g., conveyor belt, etc.).

Solar cell substrate 604 is then positioned in the field of view of electromagnetic sensor 606 and illuminated by an electromagnetic source 607 that transmits at least one wavelength above about 1100 nm. The inventors believe that these wavelengths are optimized for detection of the highly doped region.

In general, the sensor may be selected such that they are sensitive to the wavelengths of the appropriate illumination source. In this configuration, video cameras are used with appropriate CCD chips. The resolution needs to be sufficient to resolve all relevant features of the pattern used for the alignment. The field of view needs to be large enough to image all relevant features of the pattern used for the alignment. Band pass filters optimized to the wavelength range of the illumination source may be used to filter out background radiation and obtain better contrast.

As the highly doped region pattern is determined, the axial (x and y) and angular position (theta) of known landmarks within the pattern are calculated. For example, if the set of highly doped regions is patterned as a set of busbars and fingers, the set of fiducial marks or known landmarks may be specific intersections of a busbar to a finger at well defined locations.

Once determined, the locations of the landmarks within the set of highly doped regions are transmitted to metal deposition apparatus 610 (such as a screen printer which may include squeegee 612). After solar cell substrate 604 is positioned in metal deposition apparatus 610 (here via turntable 608), the printing screen of metal deposition apparatus 610 is adjusted axially and angularly in order to align the set of metal contacts to be deposited onto the set of highly doped regions. Alternately, the axial and angular position of the printing screen remains fixed and solar cell substrate 604 itself is adjusted.

After deposition of the metal contacts onto the set of highly doped regions using squeegee 612, the solar cell substrate with the set of metal contacts [not shown] is then positioned on substrate outtake transport apparatus 611, where it may be transported for additional processing.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

As will be understood by one skilled in the art, for any and all purposes, particularly in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. In addition, the terms "dopant or doped" and "counter-dopant or counter-doped" refer to a set of dopants of opposite types. That is, if the dopant is p-type, then the counter-dopant is n-type. Furthermore, unless otherwise dopant-types may be switched.

All publications, patent applications, issued patents, and other documents referred to in this specification are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

For the purposes of this disclosure and unless otherwise specified, "a" or "an" means "one or more." All patents, applications, references and publications cited herein are incorporated by reference in their entirety to the same extent as if they were individually incorporated by reference. In addition, the word set refers to a collection of one or more items or objects.

Advantages of the invention include methods for distinguishing a set of highly doped regions from a set of lightly doped regions on a silicon substrate. Additional advantages include the production of efficient solar cells.

Having disclosed exemplary embodiments and the best mode, modifications and variations may be made to the disclosed embodiments while remaining within the subject and spirit of the invention as defined by the following claims.

What is claimed is:

1. A method of distinguishing a set of highly doped regions from a set of lightly doped regions on a silicon substrate, comprising:
   providing the silicon substrate, the silicon substrate configured with the set of lightly doped regions and the set of highly doped regions, the substrate further having a first surface and a second surface;
   illuminating the first surface with an electromagnetic radiation from a source, the electromagnetic radiation having a wavelength above 1100 nm; and,
   measuring the electromagnetic radiation transmitted through the substrate with a sensor on the second surface in order to determine an absorption of a region of the set, wherein for any wavelength above 1100 nm, the measured absorption of the wavelength in the lightly doped regions is substantially less than the measured absorption of the wavelength in the heavily doped regions.

2. The method of claim 1, further comprising the step of depositing a set of metal contacts on the set of highly doped regions after illuminating the silicon substrate with the electromagnetic radiation.

3. The method of claim 1, wherein the set of highly doped regions comprises a dopant concentration of $10^{18}$ to $10^{20}$ atoms/cm$^3$.

4. The method of claim 1, wherein the set of highly doped regions comprises one of a p-type dopant and an n-type dopant.

5. The method of claim 1, wherein the set of lightly doped regions comprises a dopant concentration of $10^{14}$ to $10^{17}$ atoms/cm$^3$.

6. The method of claim 1, wherein the set of lightly doped regions comprises one of a p-type dopant and an n-type dopant.

7. The method of claim 1, wherein the wavelength of light above about 1100 nm is transmitted with a white light radiation source.

8. The method of claim 7, wherein the white light radiation source is a halogen tungsten lamp.

9. The method of claim 1, wherein the sensor is an infrared detector.

10. A method of distinguishing a set of highly doped regions from a set of lightly doped regions on a silicon substrate, comprising:
    providing the silicon substrate, the silicon substrate configured with the set of lightly doped regions and the set of highly doped regions, the substrate further having a first surface and a second surface;
    illuminating the first surface with an electromagnetic radiation from a source, the electromagnetic radiation having a wavelength between about 1100 nm and about 1700 nm; and
    measuring the electromagnetic radiation transmitted through the substrate with a sensor on the second surface in order to determine an absorption of a region of the set, wherein for any wavelength between about 1100 nm and about 1700 nm, the measured absorption of the wavelength in the lightly doped regions is substantially less than the measured absorption of the wavelength in the heavily doped regions.

* * * * *